United States Patent [19]

Hejndorf

[11] Patent Number: Plant 7,460

[45] Date of Patent: Mar. 5, 1991

[54] MINIATURE ROSE PLANT NAMED RUICARMI

[75] Inventor: Poul Hejndorf, Brabrand, Denmark

[73] Assignee: DeRuiter's Nieuwe Rozen B.V., Netherlands

[21] Appl. No.: 392,578

[22] Filed: Aug. 11, 1989

[51] Int. Cl.[5] ..... A01H 5/00

[52] U.S. Cl. ..... Plt./9

[58] Field of Search ..... Plt. 9, 10

[56] References Cited

U.S. PATENT DOCUMENTS

P.P. 5,770 7/1986 DeRuiter ..... Plt. 10

*Primary Examiner*—James R. Feyrer

*Attorney, Agent, or Firm*—Christie, Parker & Hale

[57] ABSTRACT

A new variety of miniature rose having light pink flowers produced on a good pot forcing plant also suitable for growing outdoor in gardens.

2 Drawing Sheets

SUMMARY OF THE INVENTION

The present invention relates to a new and distinct variety of rose plant of the miniature rose class, which was discovered by me as a natural mutation in a controlled planting of the variety known as "Ruimired", U.S. Plant Pat. No. 5,970, the disclosure of which is incorporated herein by reference, and which it differs from in flower coloring. The varietal denomination of the new variety is "Ruicarmi".

Among the novel characteristics possessed by this new variety which distinguishes it from its parents and all other varieties of which I am aware are its attractive light pink flowers borne on a plant suitable for production of flowering pot plants and as garden plants grown outdoor. "Ruicarmi" can be reproduced through propagation by cuttings or by grafting. Flowers of the new variety are long lasting on the plant. Asexual reproduction by budding and propagation by cuttings of the new variety as performed in Sabro, Denmark, shows that the foregoing and other distinguishing characteristics come true to form and are established and transmitted through succeeding propagation.

The accompanying drawings show typical specimens of the vegetative growth and flowers of the new variety in different stages of development and depicted in color as nearly true as it is reasonably possible to make the same in a color illustration of this character.

BRIEF DESCRIPTION OF THE DRAWINGS

FIG. 1 is an illustration of a plant of the new variety showing flowering and growth habit; and FIG. 2 is an illustration showing details of the new miniature rose variety.

DESCRIPTION OF PREFERRED EMBODIMENT

The following is a detailed description of my new variety, with color terminology in accordance with The Royal Horticultural Society Colour Chart (R.H.S.C.C.) and horticultural terminology in accordance with standard terminology used in UPOV-approved horticultural guidelines. The terminology used in color description herein refers to plate numbers in the aforementioned color chart.

Parentage: Mutation of "Ruimired".

Class: Miniature.

As can be seen in the accompanying illustrations, FIG. 1 shows one sample of flowering plant of "Ruicarmi" depicting the pot plant habit of growth and flowering. Since flowering is nearly continuous, the floriferous "Ruicarmi" pot plant can remain attractively in bloom for long periods when given proper care and culture.

FIG. 2 shows details of the new variety "Ruicarmi". In the illustration there is shown the top of a young shoot, 1; compound three, five and seven leaflet leaves, 2, 3, and 4, respectively; a stem, 5; flower buds, 6, after sepals separate, and, 7, after petals begin to unfurl; a flower, 8, about one-half open; and a flower, 9, fully open. Also shown are flower stems, 10, 11, and 12, with reproductive organs but without petals.

The following further horticultural observations were made of specimens grown outdoor in Holland.

FLOWER

Blooming habit: Nearly continuous.

A. Bud:

(1) *Size.*—Medium.

(2) *Form.*—Pointed, ovate.

(3) *Color.*—As sepals divide, bud color is near 49A with yellow coloring toward base, coloring of outer petals may show variation in pink tonality with margins sometimes lighter and deeper tones where petals bunch.

(4) *Sepals.*—About same length as bud, simple to foliated.

(5) *Penduncle.*—Length — about 3 to 4 cm. Aspect — straight. Strength — erect. Color — medium green.

B. Bloom:

*Flower.*—Average size for miniature; viewed from top — rounded; viewed from side: (A) upper part of fully opened flower — flat; (B) lower part of fully opened flower — convex.

(1) *Size.*—Average size when fully expanded — about 3.5 to 4 cm.

(2) *Borne.*—Singly, one to a stem and in small clusters.

(3) *Form.*—Ovoid at first, becoming flat then convex at maturity. Petals may reflex to points or roll under at margin.

(4) *Petalage.*—Number of petals under normal conditions — about 20 to 30, fully double.

(5) *Color.*—After sepals fall and petals unfurl, predominant flower color viewing petals' top surface is light pink near 49A to 56A with deeper hues where petals bunch and some lightening at margins of outer petals. Color is substantially stable and with some lightening of margins of outer petals. As blooms mature, flower coloring tends to lighten. On reverse, petals are lighter toned and may be imbued with light yellow or apricot underlay toward point of petal attachment, approaching near 4D on the petals top surface and somewhat lighter at the undersurface. Overall tonality from a distance is an attractive light pink.

(6) *Flowering.*—Medium number of flowers.

(7) *Flower pedicel.*—Few hairs or prickles.

C. Petals:

(1) *Texture.*—Medium.

(2) *Appearance.*—Inside velvety and outside satiny.

(3) *Form.*—Broad obovate.

(4) *Arrangement.*—Regularly arranged, imbricated.

(5) *Petaloids in center.*—Few.

(6) *Persistence.*—Drop off cleanly.

(7) *Fragrance.*—Slight to none.

(8) *Lasting quality.*—Long lasting quality on plant.

REPRODUCTIVE ORGANS

A. Stamens, filaments and anthers:

*Arrangement and color.*—Regularly arranged around styles; color — filaments pale yellow.

B. Pollen:

*Color.*—yellow.

C. Styles: Even, medium length, bunched little or no hairiness in upper half.

D. Stigma: Full, reddish, above anthers.

E. Hips: Small, pear-shaped.

PLANT

A. Form: Upright to bushy.

B. Growth: Vigorous; height attained — about 20 to 30 cm.

C. Foliage: Compound 3, 5 and 7 leaflets.

(1) *Size.*—Small to medium for a miniature.

(2) *Quantity.*—Abundant.

(3) *Color.*—Foliage at time of first flowering — medium green.

(4) *Shape.*—Oval, pointed.

(5) *Texture.*—Upper side is weakly glossy; under side is matte.

(6) *Edge.*—Serrate.

(7) *Serration.*—Ordinary, acuminate apices.

(8) *Leaf stem.*—Color — medium green.

(9) *Stipules.*—Medium length, slightly bearded, light green, distinct auricle.

(10) *Leaflet.*—Cross section — flat; terminal leaflet — length of blade, short to very short; maximum width, narrow; shape of base, rounded; petiole length — short.

D. Wood:

(1) *New wood.*—Color — reddish brown (purple).

(2) *Old wood.*—Color — medium green.

E. Prickles (thorns):

(1) *Prickles.*—Present, quantity (main stalk) — ordinary; on laterals from stalk — few; form — straight and slanted downward; shape, upper side — flat; shape, lower side — concave; number of short prickles ($\leqq 5$ mm) — medium; number of long prickles ($>5$ mm) — very few; color — tan to light or pale pink; position — irregular.

(2) *Bristles and glandular hairs.*—Few to none.

F. Winter hardiness: Needs protection outdoors in severe climates.

I claim:

1. A new and distinct variety of rose plant of the miniature rose class, substantially as shown and described, characterized particularly by a plant suitable for growing in pots and outdoor in gardens and by attractive light pink flowers which are long lasting on the plant.

* * * * *

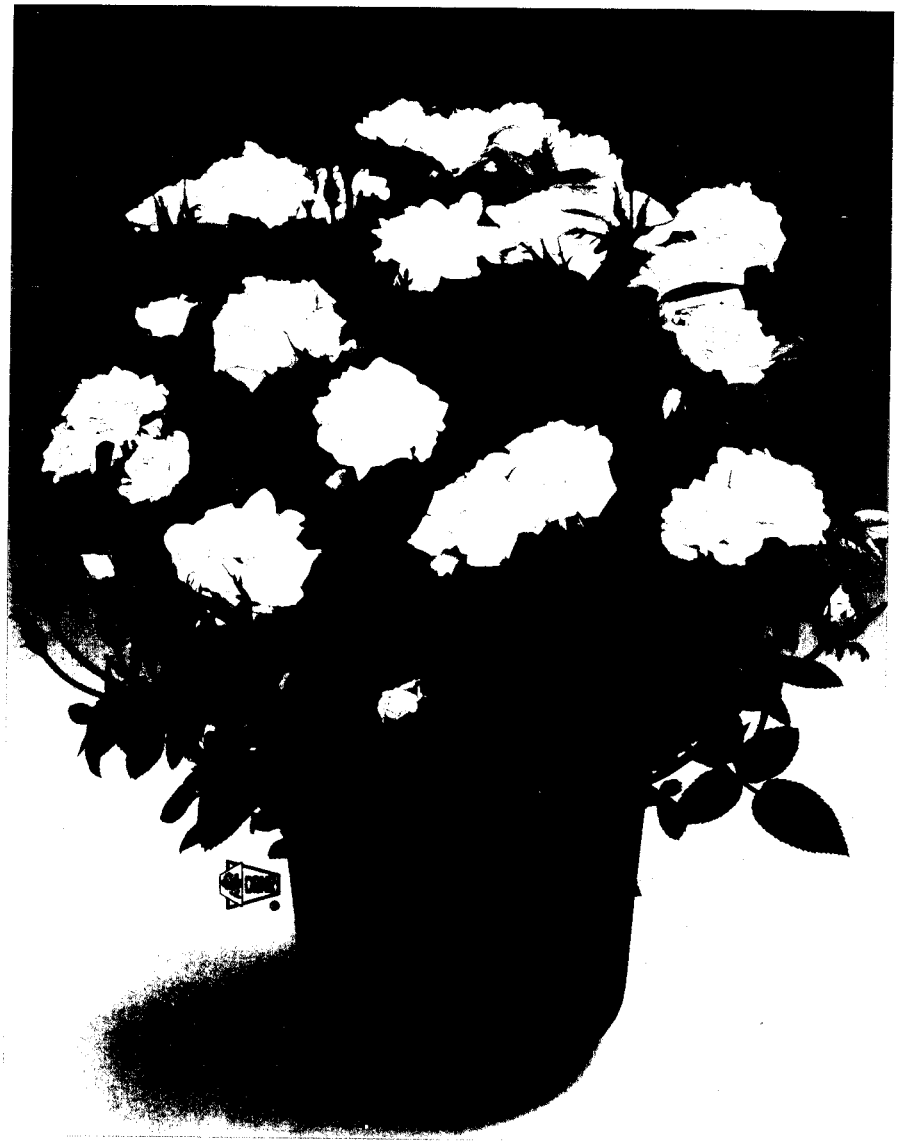

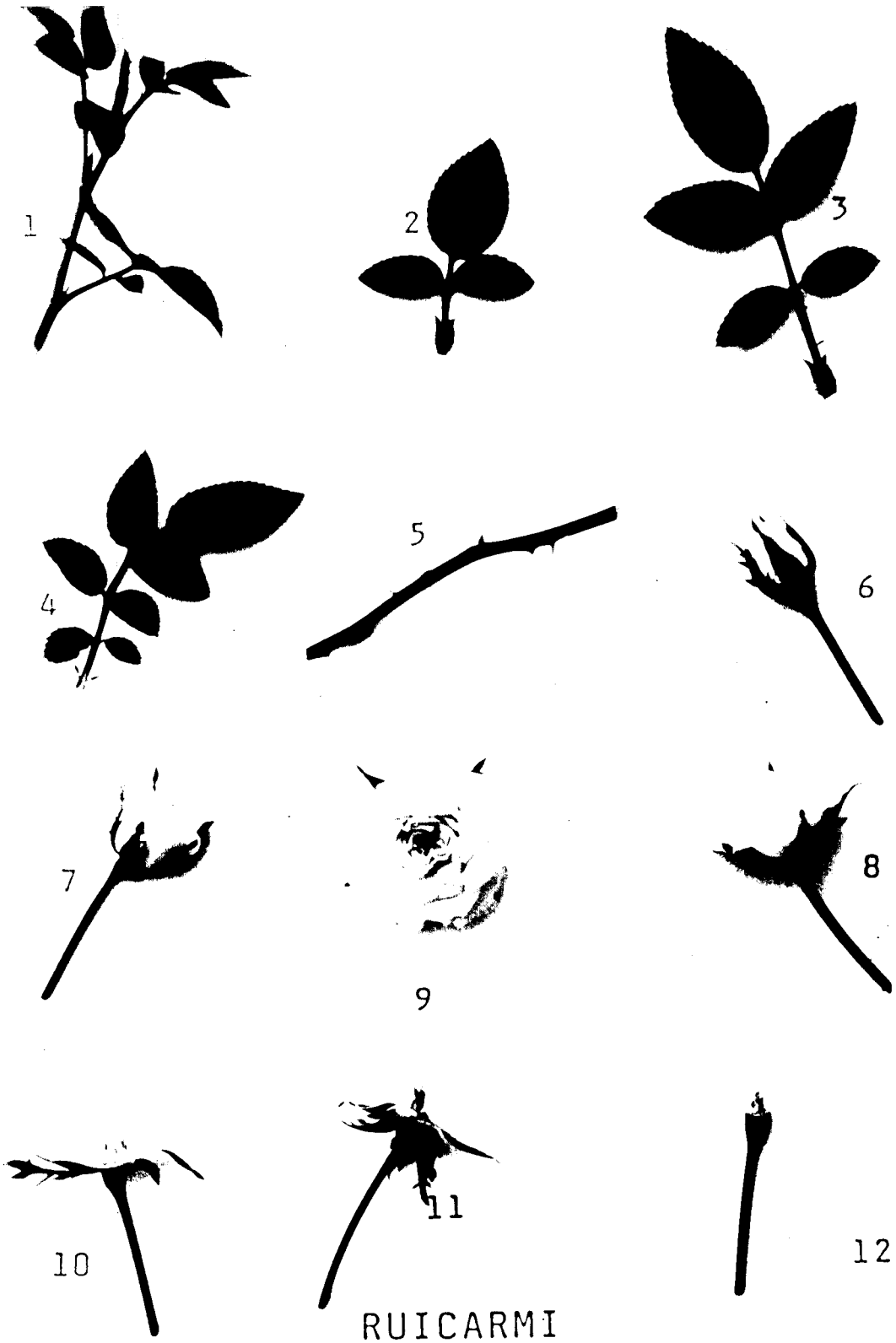
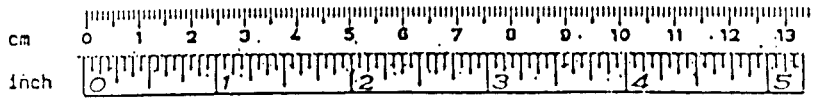
2-12

UNITED STATES PATENT AND TRADEMARK OFFICE

CERTIFICATE OF CORRECTION

PATENT NO. : Plant 7,460

DATED : March 5, 1991

INVENTOR(S) : Poul Hejndorf

It is certified that error appears in the above-identified patent and that said Letters Patent is hereby corrected as shown below:

Column 2, line 20, before "FLOWER" insert -- 1. --.

Column 3, line 29, before "REPRODUCTIVE ORGANS" insert -- 2. --.

Column 3, line 40, before "PLANT" insert -- 3. --.

Signed and Sealed this

Twentieth Day of October, 1992

*Attest:*

*Attesting Officer*

DOUGLAS B. COMER

*Acting Commissioner of Patents and Trademarks*